United States Patent [19]

Powell et al.

[11] Patent Number: 5,463,145
[45] Date of Patent: Oct. 31, 1995

[54] PROCESS FOR PREPARING 1,3-PROPANEDIOL

[75] Inventors: Joseph B. Powell; Lynn H. Slaugh, both of Houston; Thomas C. Forschner, Richmond; Thomas C. Semple, Friendswood; Paul R. Weider, Houston, all of Tex.

[73] Assignee: Shell Oil Company, Houston, Tex.

[21] Appl. No.: 316,673

[22] Filed: Sep. 30, 1994

[51] Int. Cl.$^6$ ............ C07C 27/20; C07C 45/49; C07C 47/17
[52] U.S. Cl. ............ 568/867; 502/167; 502/24; 502/28; 560/179; 568/451; 568/454; 568/496; 568/822; 568/852; 568/854; 568/862; 568/882
[58] Field of Search ............ 568/451, 454, 568/496, 867, 882, 854, 844, 862, 852, 867, 882; 252/413; 502/167; 560/179

[56] References Cited

U.S. PATENT DOCUMENTS

| | | | |
|---|---|---|---|
| 3,168,553 | 2/1965 | Slaugh | 260/497 |
| 3,456,017 | 7/1969 | Smith | 260/602 |
| 3,463,819 | 8/1969 | Smith | 260/602 |
| 3,687,981 | 8/1972 | Lawrence | 260/340.7 |
| 4,137,240 | 1/1979 | Peterson | 260/340.7 |
| 4,255,279 | 3/1981 | Spohn | 252/413 |
| 4,404,119 | 9/1983 | Lagace | 252/413 |
| 4,873,378 | 10/1989 | Murphy | 568/867 |
| 4,873,379 | 10/1989 | Murphy | 568/867 |
| 4,973,741 | 11/1990 | Beavers | 560/179 |
| 5,030,766 | 7/1991 | Briggs | 568/496 |
| 5,053,562 | 10/1991 | Tau | 568/867 |
| 5,210,318 | 5/1993 | Briggs | 568/496 |
| 5,225,387 | 7/1993 | Briggs | 502/167 |
| 5,256,827 | 10/1993 | Slaugh | 568/454 |
| 5,304,686 | 4/1994 | Slaugh et al. | 568/496 |
| 5,321,168 | 6/1994 | Roussel | 568/882 |
| 5,334,798 | 8/1994 | Haas et al. | 568/862 |
| 5,364,984 | 11/1994 | Arntz et al. | 568/862 |
| 5,364,987 | 11/1994 | Haas et al. | 568/866 |

OTHER PUBLICATIONS

Falbe, Carbon monoxide In Organic Synthesis, Springer–Verlag (1970), pp. 14–15.
Falbe, New Synthesis With Carbon Monoxide, Springer–Verlag (1980), p. 131.

*Primary Examiner*—Werren B. Lone

[57] ABSTRACT

1,3-Propanediol is prepared in a process comprising the steps of:

contacting, in an essentially non-water-miscible organic solvent, ethylene oxide with carbon monoxide and hydrogen in the presence of a catalytic amount of a non-phosphine-ligated cobalt compound and an effective amount of a lipophilic quaternary phosphonium salt promoter at a temperature within the range of about 50° to about 100° C. and a pressure within the range of about 500 to about 5000 psig, to produce an intermediate product mixture comprising less than 15 wt % 3-hydroxypropanal;

adding an aqueous liquid to said intermediate product mixture and extracting into said aqueous liquid a major portion of the 3-hydroxypropanal at a temperature less than about 100° C. to provide an aqueous phase comprising 3-hydroxypropanal in greater concentration than the concentration of 3-hydroxypropanal in the intermediate product mixture, and an organic phase comprising at least a portion of the cobalt compound and at least a portion of the lipophilic quaternary phosphonium salt;

contacting the aqueous phase comprising 3-hydroxypropanal with hydrogen in the presence of a hydrogenation catalyst at a pressure of at least about 100 psig and a temperature during at least a portion of the hydrogenation step of at least 40° C. to provide a hydrogenation product mixture comprising 1,3-propanediol.

11 Claims, 1 Drawing Sheet

PROCESS FOR PREPARING 1,3-PROPANEDIOL

BACKGROUND OF THE INVENTION

This invention relates to the preparation of 1,3-propanediol. In one aspect, the invention relates to a cobalt-catalyzed process for manufacturing 1,3-propanediol in high yields without the use of a phosphine-ligated cobalt catalyst.

1,3-propanediol (PDO) is an intermediate in the production of polyesters for fibers and films. It is known to prepare PDO in a two-step process involving (1) the cobalt-catalyzed hydroformylation (reaction with synthesis gas, $H_2/CO$) of ethylene oxide to intermediate 3-hydroxypropanal (HPA) and (2) subsequent hydrogenation of the HPA to PDO. The initial hydroformylation process can be carried out at temperatures greater than 100° C. and at high $H_2/CO$ pressures to achieve practical reaction rates. The resulting product mixture is, however, rather unselective for HPA.

In an alternate synthesis method, the cobalt catalyst is used in combination with a phosphine ligand to prepare HPA with greater selectivity and at lower temperature and pressure. However, the use of a phosphine ligand adds to the cost of the catalyst and increases the complexity of catalyst recycle.

It would be desirable to prepare HPA in a low temperature, selective process which did not require a phosphine ligand with the cobalt catalyst.

It is therefore an object of the invention to provide an economical process for the preparation of 1,3-propanediol which does not require the use of a phosphine-ligated catalyst for preparation of the HPA intermediate. It is a further object of the invention to provide a process for the preparation of 1,3-propanediol in which essentially all of the cobalt catalyst can be conveniently recycled.

SUMMARY OF THE INVENTION

According to the invention, 1,3-propanediol is prepared in a process comprising the steps of:

(a) contacting, in an essentially non-water-miscible organic solvent, ethylene oxide with carbon monoxide and hydrogen in the presence of a catalytic amount of a non-phosphine-ligated cobalt compound and an effective amount of a lipophilic quaternary phosphonium salt promoter at a temperature within the range of about 50° to about 100° C. and a pressure within the range of about 500 to about 5000 psig, under conditions effective to produce an intermediate product mixture comprising less than about 15 wt % 3-hydroxypropanal;

(b) adding an aqueous liquid to said intermediate product mixture and extracting into said aqueous liquid a major portion of the 3-hydroxypropanal at a temperature less than about 100° C. to provide an aqueous phase comprising 3-hydroxypropanal in greater concentration than the concentration of 3-hydroxypropanal in the intermediate product mixture, and an organic phase comprising at least a portion of the cobalt compound or a cobalt-containing derivative thereof and at least at least a portion of the lipophilic quaternary phosphonium salt;

(c) separating the aqueous phase from the organic phase;

(d) contacting the aqueous phase comprising 3-hydroxypropanal with hydrogen in the presence of a hydrogenation catalyst at a pressure of at least about 100 psig and a temperature during at least a portion of the hydrogenation step of at least 40° C. to provide a hydrogenation product mixture comprising 1,3-propanediol;

(e) recovering 1,3-propanediol from the hydrogenation product mixture; and (f) returning at least a portion of the organic phase comprising cobalt compound and lipophilic quaternary phosphonium salt to the process of step (a).

The process enables the production of 1,3-propanediol in high yield and selectivity without the use of a phosphine-ligated cobalt catalyst in the hydroformylation step. The process also enables the recovery and recycle of essentially all the cobalt catalyst.

DETAILED DESCRIPTION OF THE INVENTION

Figure 1:
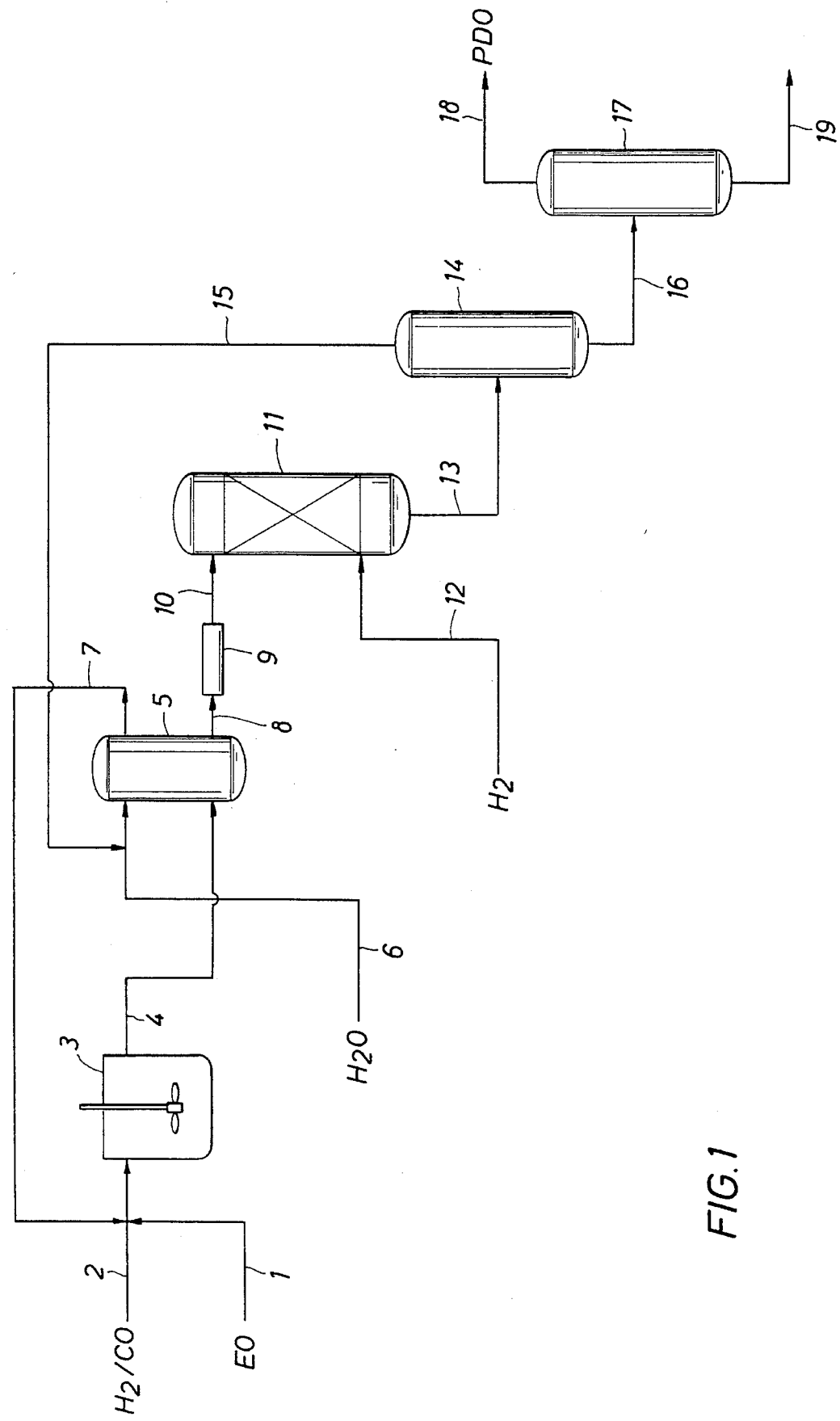
FIG. 1 is a schematic flow diagram of one embodiment of the invention 1,3-propanediol preparation process.

The invention process can be conveniently described by reference to FIG. 1. Separate or combined streams of ethylene oxide 1, carbon monoxide and hydrogen 2 are charged to hydroformylation vessel 3, which can be a pressure reaction vessel such as a bubble column or agitated tank, operated batchwise or in a continuous manner. The feed streams are contacted in the presence of a non-phosphine-ligated cobalt catalyst, i.e., a cobalt carbonyl composition which has not been prereacted with a phosphine ligand. The hydrogen and carbon monoxide will generally be introduced into the reaction vessel in a molar ratio within the range of about 1:2 to about 8:1, preferably about 1.5:1 to about 5:1.

The reaction is carried out under conditions effective to produce a hydroformylation reaction mixture comprising a major portion of 3-hydroxypropanal (HPA) and a minor portion of acetaldehyde, while maintaining the level of 3-hydroxypropanal in the reaction mixture at less than 15 wt %, preferably about 5 to about 10 wt %. (To provide for solvents having different densities, the concentration of HPA in the reaction mixture can be expressed in molarity, i.e., less than 1.5M, preferably within the range of about 0.5 to about 1M.) Generally, the hydroformylation reaction is carried out at elevated temperature less than 100° C., preferably about 60° to about 90° C., most preferably about 75° to about 85° C., and at a pressure within the range of about 500 to about 5000 psig, preferably (for process economics) about 1000 to about 3500 psig, with higher pressures generally imparting greater selectivity. The concentration of 3-hydroxypropanal in the intermediate product mixture can be controlled by regulation of process conditions such as ethylene oxide concentration, catalyst concentration, reaction temperature and residence time. In general, relatively low reaction temperatures (below about 100° C.) and relatively short residence times within the range of about 20 minutes to about 1 hour are preferred.

In the practice of the invention method, it is possible to achieve HPA yields (based on ethylene oxide conversion of greater than 80%, with formation of more than 7 wt % HPA in the dilute hydroformylation product mixture, at rates greater than 30 $h^{-1}$. (Catalytic rates are referred to herein in terms of "turnover frequency" or "TOF" and are expressed in units of moles per mole of cobalt per hour, or $h^{-1}$.) Reported rates are based on the observation that, before a majority of the ethylene oxide is converted, the reaction is essentially zero-order in ethylene oxide concentration and proportional to cobalt concentration.

The hydroformylation reaction is carried out in a liquid solvent inert to the reactants. By "inert" is meant that the solvent is not consumed during the course of the reaction. In general, ideal solvents for the phosphine ligand-free process (a) will exhibit low to moderate polarity such that 3-hydroxypropanal intermediate will be solubilized to the desired concentration of at least about 5 wt % under hydroformylation conditions, while significant solvent will remain as a separate phase upon water extraction, (b) will solubilize carbon monoxide, and (c) will be essentially non-water-miscible. By "essentially non-water-miscible" is meant that the solvent has a solubility in water at 25° C. of less than 25 wt % so as to form a separate hydrocarbon-rich phase upon water extraction of HPA from the hydroformylation reaction mixture. Preferably, this solubility is less than about 10 wt %, most preferably less than bout 5 wt %. The solubilization of carbon monoxide in the selected solvent will generally be greater than 0.15 v/v (1 atm, 25° C.), preferably greater than 0.25 v/v, expressed in terms of Ostwald coefficients.

The preferred class of solvents are alcohols and ethers which can be described according to the formula $$R_2—O—R_1 \qquad (1)$$

in which $R_1$ is hydrogen or $C_{1-20}$ linear, branched, cyclic or aromatic hydrocarbyl or mono- or polyalkylene oxide and $R_2$ is a linear, branched, cylic or aromatic $C_{1-20}$ hydrocarbyl, alkoxy or mono- or polyakylene oxide. The most preferred hydroformylation solvents can be described by the formula $$R_4—\overset{\overset{R_3}{|}}{\underset{\underset{R_5}{|}}{C}}—O—R_1 \qquad (2)$$

in which $R_1$ is hydrogen or $C_{1-8}$ hydrocarbyl and $R_3$, $R_4$ and $R_5$ are independently selected from $C_{1-8}$ hydrocarbyl, alkoxy and mono- or polyalkylene oxide. Such ethers include, for example, methyl-t-butyl ether, ethyl-t-butyl ether, ethoxyethyl ether, phenylisobutyl ether, diethyl ether, diphenyl ether, and diisopropyl ether. Blends of solvents such as tetrahydrofuran/toluene, tetra-hydrofuran/heptane and t-butylalcohol/hexane can also be used to achieve the desired solvent properties. The currently preferred solvent, because of the high yields of HPA which can be achieved under moderate reaction conditions, is methyl-t-butyl ether.

The catalyst is a non-phosphine-ligated cobalt carbonyl compound. Although phosphine-ligated catalysts are active for the described hydroformylation reaction, it is desirable to employ a process in which good yield and selectivity are achieved without a phosphine ligand because of the additional expense of the ligand. The cobalt catalyst can be supplied to the hydroformylation reactor in essentially any form including metal, supported metal, Raney-cobalt, hydroxide, oxide, carbonate, sulfate, acetylacetonate, salt of a fatty acid, or aqueous cobalt salt solution, for example. It may also be supplied directly as a cobalt carbonyl such as dicobaltoctacarbonyl or cobalt hydridocarbonyl. If not supplied in the latter forms, operating conditions must be adjusted such that cobalt carbonyls are formed via reaction with $H_2$ and CO, as described in J. Falbe, "Carbon Monoxide in Organic Synthesis," Springer-Verlag, N.Y. (1970). In general, conditions will include a temperature of at least 50° C. and a carbon monoxide partial pressure of at least about 100 psig. For more rapid reaction, temperatures of about 120° to 200° C. should be employed, at CO pressures of at least 500 psig. Addition of high surface area activated carbons or zeolites, especially those containing or supporting platinum or palladium metal, is known to accelerate carbonyl formation cobalt noncarbonyl precursors. The resulting catalyst is maintained under a stabilizing atmosphere of carbon monoxide, which also provides protection against exposure to oxygen. The most economical and preferred catalyst activation and reactivation (of recycled catalyst) method involves preforming the cobalt salt (or derivative) under $H_2/CO$ in the presence of the catalyst promoter employed for hydroformylation. The conversion of $Co^{2+}$ to the desired cobalt carbonyl is carried out at a temperature within the range of about 75° to about 200° C., preferably about 100° to about 140° C. and a pressure within the range of about 1000 to about 5000 psig for a time preferably less than about 3 hours. The preforming step can be carried out in a pressurized preforming reactor or in-situ in the hydroformylation reactor.

The amount of cobalt present in the reaction mixture will vary depending upon the other reaction conditions, but will generally fall within the range of about 0.01 wt % to about 1 wt %, preferably about 0.05 to about 0.3 wt %, based on the weight of the reaction mixture.

The hydroformylation reaction is carried out in the presence of a lipophilic quaternary phosphonium salt to accelerate the reaction rate without imparting hydrophilicity (water solubility) to the active catalyst. By "lipophilic" is meant that the promoter tends to remain in the organic phase after extraction of HPA with water. The quaternary phosphonium salt will be present in an amount effective to promote the hydroformylation reaction to HPA, generally an amount within the range of about 0.01 to about 0.6 moles per mole of cobalt.

Quaternary phosphonium salts include those represented by formula (1)

$$R_1—\overset{\overset{R_2}{|}}{\underset{\underset{R_4}{|}}{P^+}}—R_3A^- \qquad (1)$$

in which each R group is selected independently from unsubstituted and inertly-substituted $C_{1-25}$ linear, branched, cyclic or aromatic hydrocarbyl, alkoxy, or mono- or polyalkylene oxide, and A is a basic anion having a conjugate acid of pKa>2 such as carboxylate, phenate and hydroxide, for example. Halide anions are believed to be ineffective. Two or more of the R groups together may form a cyclic or aromatic structure. Such quaternary phosphonium salts include tetra-n-butyl phosphonium acetate, tetraoctyl phosphonium acetate, tetraphenyl phosphonium hydroxide and benzyltrimethyl phosphonium acetate.

It is generally preferred to regulate the concentration of water in the hydroformylation reaction mixture, as excessive amounts of water reduce [HPA+PDO] selectivity below acceptable levels and may induce formation of a second liquid phase. At low concentrations, water can assist in promoting the formation of the desired cobalt carbonyl catalyst species. Acceptable water levels will depend upon the solvent used, with more polar solvents generally more tolerant of higher water concentrations. For example, optimum water levels for hydroformylation in methyl-t-butyl ether solvent are believed to be within the range of about 1 to about 2.5 wt %.

Following the hydroformylation reaction, the hydroformylation reaction product mixture 4 containing 3-hydroxypropanal, the reaction solvent, 1,3-propanediol, the cobalt catalyst and a minor amount of reaction by-products, is passed to extraction vessel 5, to which an aqueous liquid, generally water and optional miscibilizing solvent, are added via 6 for extraction and concentration of the HPA for the subsequent hydrogenation step. Liquid extraction can be effected by any suitable means, such as mixer-setters, packed or trayed extraction columns or rotating disk contactors. Extraction can if desired be carried out in multiple stages. The water-containing hydroformylation reaction product mixture can be passed to a settling tank (not shown) for resolution into aqueous and organic phases. The amount of water added to the hydroformylation reaction product mixture will generally be such as to provide a water:mixture ratio within the range of about 1:1 to about 1:20, preferably about 1:5 to about 1:5. The addition of water at this stage of the reaction may have the additional advantage of suppressing formation of undesirable heavy ends. Extraction with a relatively small amount of water provides an aqueous phase which is greater than 20 wt % HPA, preferably greater than 35 wt % HPA, permitting economical hydrogenation of the HPA to PDO. The water extraction is preferably carried out at a temperature within the range of about 25° to about 55° C., with higher temperatures avoided to minimize condensation products (heavy ends) and catalyst disproportionation to inactive, water-soluble cobalt compounds. In order to maximize catalyst recovery, it is preferred to perform the water extraction under 50 to 200 psig of carbon monoxide at 25° to 55° C.

The organic phase containing the reaction solvent and the major portion of the cobalt catalyst can be recycled from the extraction vessel to the hydroformylation reaction via 7. Aqueous extract 8 is optionally passed through one or more acid ion exchange resin beds 9 for removal of any cobalt catalyst present, and the decobalted aqueous product mixture 10 is passed to hydrogenation vessel 11 and reacted with hydrogen in the presence of a hydrogenation catalyst to produce a hydrogenation product mixture 13 containing 1,3-propanediol. The hydrogenation step may also revert some heavy ends to PDO. The solvent and extractant water 14 can be recovered by distillation and recycled to the water extraction process via a further distillation (not shown) for separation and purge of light ends. PDO-containing stream 16 can be passed to one or more distillation columns 17 for recovery of PDO 18 from heavy ends 19.

Hydrogenation of the HPA to PDO can be carried out in aqueous solution at an elevated temperature during at least a portion of the hydrogenation step of about 40° C., generally within the range of about 50° to about 175° C., under a hydrogen pressure of at least about 100 psig, generally within the range of about 200 to about 2000 psig. The reaction is carried out in the presence of a hydrogenation catalyst such as any of those based upon Group VIII metals including nickel, cobalt, ruthenium, platinum and palladium, as well as copper, zinc and chromium and mixtures and alloys thereof. Nickel catalysts, including bulk, supported and fixed-bed forms, provide acceptable activities and selectivities at moderate costs. Highest yields are achieved under slightly acidic reaction conditions.

Commercial operation will preferably include efficient cobalt catalyst recovery with essentially complete recycle of cobalt to the hydroformylation reaction. The preferred catalyst recovery process involves two steps, beginning with the above-described water extraction of HPA from the hydroformylation product mixture. A majority of the cobalt catalyst will remain in the organic phase, with the remaining cobalt catalyst passing into the water phase. This organic phase can be recycled to the hydroformylation reactor, with optional purge of heavy ends. Optional further decobalting of catalyst in the water layer can be effected by suitable method such as complete or partial oxidation of cobalt followed by precipitation and filtration, distillation, deposition on a solid support, or extraction using a suitable extractant, preferably prior to final cobalt removal by ion exchange (9).

The invention process permits the selective and economical synthesis of PDO at moderate temperatures and pressures without the use of a phosphine ligand for the hydroformylation catalyst. The process involves preparation of a reaction product mixture dilute in HPA, then concentration of this HPA by water extraction for subsequent hydrogenation of HPA to PDO.

EXAMPLE 1

This experiment illustrates the use of a quaternary phosphonium salt as a promoter of cobalt-catalyzed hydroformylation of ethylene oxide. 0.87 g of dicobaltoctacarbonyl, 1.5 g toluene, 2.0 g deionized water and 146 g methyl-t-butyl ether (MTBE) containing 0.2 wt % water were preheated for one hour in a 300 ml bolted-head stirred reactor at 80° C. under 600 psig $H_2$ and 900 psig 1:1 $CO/H_2$ synthesis gas. 10 g ethylene oxide (EO) were added to initiate the hydroformylation reaction. Samples were withdrawn for periodic analysis by capillary gas chromatography to measure 3-hydroxypropanal (HPA) hydroformylation reaction product. Sampling after about 40% conversion of EO indicated formation of 3.3 wt % HPA, at a rate (TOF) of 18 $h^{-1}$.

The experiment was repeated with addition of various amounts (based on cobalt) of tetra-n-butylphosphonium acetate promoter. Results are shown in Table 1. For intermediate amounts of promoter, hydroformylation was accelerated, with highest rates for $M^+/Co$ ratios of about 0.05 to about 0.3

TABLE 1

| Run | $M^+CO$ | $H_2O$ (wt %) | HPA (wt %) | HPA Rate ($h^{-1}$) |
| --- | --- | --- | --- | --- |
| 1 | 0.00 | 1.5 | 3.3 | 18 |
| 2 | 0.01 | 1.5 | 3.3 | 25 |
| 3 | 0.03 | 1.5 | 2.6 | 20 |
| 4 | 0.07 | 1.5 | 5.7 | 40 |
| 5 | 0.21 | 0.2 | 4.3 | 44 |
| 6 | 0.24 | 2.0 | 5.0 | 34 |
| 7 | 0.37 | 1.5 | 4.3 | 33 |
| 8 | 0.55 | 1.5 | 3.2 | 17 |
| 9 | 0.59 | 1.5 | 4.2 | 16 |

EXAMPLE 2

This example illustrates water extraction of cobalt catalyst under a carbon monoxide atmosphere in the presence of a lipophilic phosphonium acetate promoter. The reaction mixture from Run 6 of Example 1 was extracted with 30 g of deionized water under 200 psig carbon monoxide at 25° C. 94.83 g of upper organic layer containing 2184 ppmw cobalt were isolated. 24.90 g of lower aqueous extract (containing most of the HPA product) were recovered and were found to contain 88 ppmw cobalt. These results correspond to 98.5% of total cobalt separated from aqueous product and remaining with the organic layer after extraction.

EXAMPLE 3

This experiment illustrates recycle of cobalt catalyst in lipophilic phosphonium acetate-promoted hydroformylation. 10.875 g of dicobaltoctacarbonyl, 7 g of 70% tetra-n-butylphosphonium acetate, 18.75 g toluene (marker), 25 g deionized water and 1838.0 g MTBE were charged to a 1-gallon bolted-head stirred reactor and heated under 2000 psig $H_2$ and 800 psig Co. After 1 hour, 123 g of ethylene oxide (EO) were added to initiate reaction. 1:1 $CO/H_2$ synthesis gas was added to replenish that depleted as hydroformylation progressed. The reaction was terminated after 50 minutes, with formation of HPA product at a rate of 39 $h^{-1}$. 375 g of deionized water were added to extract HPA at 38° C. under 200 psig 1:1 synthesis gas. 495 g of aqueous extract were recovered, yielding HPA product corresponding to 66% of EO consumed during reaction. Less than 7% of the cobalt catalyst was extracted into the aqueous phase.

The aqueous extract was removed from the reaction, and for subsequent cycles the remaining organic phase was reheated under synthesis gas (2.6 $H_2/CO$) for one hour, and 120–130 g of EO were added to perform recycle reactions, through 12 reaction cycles. Results are shown in Table 2.

HPA product in water extracts, as shown by gas chromatographic analysis, corresponded to yields (based upon EO consumed) of 70–89% at zero-order hydroformylation rates of 30–45 $h^{-1}$. Hydroformylation rates remained essentially constant for subsequent recycles, relative to the observed variability in rate measurements. Cobalt recycle (% total cobalt retained in organic phase after water extraction) in the organic phase ranged from 93 to 99%. Less than 15 ppmw phosphorus as the tetra-n-butylphosphonium promoter partitioned into the aqueous phase.

These experiments demonstrate the convenience of recycle of the cobalt catalyst with the organic layer following water extraction for separation from HPA product, in the presence of the lipophilic phosphonium acetate promoter. The recycle catalyst largely retains its catalytic activity and selectivity. Only minor amounts of promoter are lost to the aqueous phase upon extraction.

TABLE 2

| Cycle # | HPA Rate ($h^{-1}$) | Min. HPA % Yield | Co Recycle (%, UL) | P Loss (ppm) |
|---|---|---|---|---|
| 1 | 38.78 | 66.15 | 93.2 | 13 |
| 2 | 32.90 | 77.86 | 97.9 | NA |
| 3 | 31.80 | 74.43 | 98.7 | <15 |
| 4 | 35.70 | 80.01 | 99.5 | <15 |
| 5 | 32.94 | 78.76 | 99.5 | 16 |
| 6 | 32.21 | 76.16 | 98.0 | <15 |
| 7 | 31.93 | 71.14 | 98.7 | <15 |
| 8 | 38.33 | 78.57 | 96.6 | <15 |
| 9 | 36.48 | 76.50 | 96.9 | <15 |
| 10 | 36.49 | 72.03 | 94.6 | <15 |
| 11 | 37.44 | 74.98 | 97.3 | 14 |
| 12 | 42.66 | 89.02 | 96.3 | 10 |

EXAMPLE 4

Example 1 was repeated with addition of 0.8 g of tetraoctylphosphonium acetate promoter, for a ratio of 0.29 moles promoter per mole of cobalt. At approximately 40% conversion, 3.19 wt % HPA had been formed at a rate of 27.9 $h^{-1}$, or a 50% rate increase over that observed in the absence of promoter in Example 1, Run 1. Ultimately, 8.1% HPA was formed at 90% conversion.

Following the reaction, the reaction product mixture was cooled to room temperature. 30.5 g of deionized water were added for extraction of HPA under 600 psig synthesis gas. After minutes, mixing was terminated and 33.3 g of an aqueous product layer containing 27% HPA were isolated. The aqueous layer contained 57 ppm cobalt, or only 1% of the total cobalt charged. The upper organic layer (110.5 g) was analyzed to contain 0.19 wt % cobalt, or negligible loss relative to the initial cobalt charge. Recycle of 99% of the cobalt catalyst with the organic layer represents reduction in cobalt loss by a factor of 23, relative to that observed with sodium acetate promotion in Example 2.

We claim:

1. A process for preparing 1,3-propanediol comprising the steps of:

(a) contacting, in an essentially non-water-miscible organic solvent, ethylene oxide with carbon monoxide and hydrogen in the presence of an effective amount of a non-phosphine ligated cobalt hydroformylation catalyst and an effective amount of a lipophilic quaternary phosphonium salt promoter, at a temperature within the range of about 50° to about 100° C. and a pressure within the range of about 500 to about 5000 psig, under reaction conditions effective to produce an intermediate product mixture comprising less than 15 wt % 3-hydroxypropanal;

(b) adding an aqueous liquid to said intermediate product mixture and extracting into said aqueous liquid at a temperature less than about 100° C. a major portion of the 3-hydroxypropanal, to provide an aqueous phase comprising 3-hydroxypropanal in greater concentration than the concentration of 3-hydroxypropanal in said intermediate product mixture, and an organic phase comprising at least a portion of the cobalt catalyst or a cobalt-containing derivative thereof and at least a portion of the lipophilic quaternary phosphonium salt;

(c) separating the aqueous phase from the organic phase;

(d) contacting the aqueous phase comprising 3-hydroxypropanal with hydrogen in the presence of a hydrogenation catalyst at a pressure of at least about 100 psig and a temperature during at least a portion of the hydrogenation step of at least about 40° C. to provide a hydrogenation product mixture comprising 1,3-propanediol;

(e) recovering 1,3-propanediol from the hydrogenation product mixture; and (f) returning at least a portion of the organic phase comprising cobalt catalyst or a cobalt-containing derivative thereof and lipophilic quaternary phosphonium salt to the process of step (a).

2. The process of claim 1 in which the solvent of step (a) comprises an ether.

3. The process of claim 1 in which the 3-hydroxypropanal in the intermediate product mixture is maintained at a level within the range of about 5 to about 10 wt %.

4. The process of claim 1 in which step (a) is carried out at a temperature within the range of about 60° to about 90° C.

5. The process of claim 1 in which step (a) is carried out at a pressure within the range of about 1000 to about 3500 psig.

6. The process of claim 1 in which the lipophilic quaternary phosphonium salt comprises a tetrahydrocarbyl phosphonium acetate.

7. The process of claim 3 in which the solvent has a solubility in water less than 10 wt % at 25° C.

8. The process of claim 1 in which the solvent of step (a) comprises methyl-t-butyl ether.

9. The process of claim 1 in which the lipophilic phosphonium salt comprises tetra-n-butyl phosphonium acetate.

10. The process of claim 1 in which step (b) is carried out under carbon monoxide.

11. A process for preparing 1,3-propanediol comprising the steps of:

(a) reacting ethylene oxide, carbon monoxide and hydrogen in a solvent comprising methyl-t-butyl ether at a temperature of about 60° to about 90° C. in the presence of a catalytic amount of a non-phosphine-ligated cobalt carbonyl compound and a promoting amount of a lipophilic quaternary phosphonium acetate, under hydroformylation conditions effective to produce an intermediate product mixture comprising 3-hydroxypropanal in a concentration within the range of about 5 to about 10 wt %;

(b) adding an aqueous liquid to said intermediate product mixture in an amount within the range of about 10 to about 25 wt % based on the weight of the intermediate product mixture, and permitting the water-containing intermediate product mixture to resolve into an aqueous phase comprising 3-hydroxypropanal in a concentration of at least about 35 wt %, and an organic phase comprising a major portion of the cobalt carbonyl compound;

(c) separating the aqueous phase and the organic phase and subsequently removing any cobalt carbonyl compound from the aqueous phase;

(d) contacting the aqueous phase comprising 3-hydroxypropanal with hydrogen in the presence of a hydrogenation catalyst at a pressure of at least about 100 psig and a temperature of at least about 40° C. to provide a hydrogenation product mixture comprising 1,3-propanediol;

(e) recovering 1,3-propanediol from the hydrogenation product mixture; and (f) returning at least a portion of the organic phase comprising cobalt carbonyl compound and lipophilic phosphonium acetate to the process of step (a).

* * * * *